United States Patent [19]

Degen et al.

[11] Patent Number: 5,380,903
[45] Date of Patent: Jan. 10, 1995

[54] PROCESS FOR THE PREPARATION OF ORGANOCHLOROSILANES

[75] Inventors: Bruno Degen, Much; Elke Licht, Leverkusen; Manfred Schulze, Leichlingen; Gebhard Wagner, Odenthal; Klaus-Peter Minuth, Düsseldorf, all of Germany

[73] Assignee: Bayer Aktiengesellschaft, Leverkusen, Germany

[21] Appl. No.: 214,731

[22] Filed: Mar. 17, 1994

[30] Foreign Application Priority Data

Mar. 24, 1993 [DE] Germany ............... 4309556
Dec. 16, 1993 [DE] Germany ............... 4342910

[51] Int. Cl.$^6$ ............................................. C07F 7/16
[52] U.S. Cl. ............................................. 556/472
[58] Field of Search ........................................ 556/472

[56] References Cited

U.S. PATENT DOCUMENTS

| | | |
|---|---|---|
| 2,380,997 | 8/1945 | Patnode ............... 556/472 |
| 2,803,521 | 8/1957 | Nitzsche et al. ............... 556/472 |
| 4,218,387 | 8/1980 | Maas et al. ............... 556/472 |
| 4,450,282 | 5/1984 | Ritzer et al. ............... 556/472 |
| 4,895,969 | 6/1990 | Feldner et al. ............... 556/472 |
| 5,239,102 | 8/1993 | Webb et al. ............... 556/472 |
| 5,243,061 | 9/1993 | Webb et al. ............... 556/472 |
| 5,250,716 | 10/1993 | Mui ............... 556/472 |
| 5,274,158 | 12/1993 | Webb et al. ............... 556/472 |

FOREIGN PATENT DOCUMENTS 0372341 6/1990 European Pat. Off. .
950124 10/1956 Germany .

*Primary Examiner*—Paul F. Shaver
*Attorney, Agent, or Firm*—Sprung Horn Kramer & Woods

[57] ABSTRACT

Metallic silicon for the Rochow-Synthesis is reduced to particles measuring at least 5 mm in their smallest dimension and 15 mm in their largest dimension, cooling the silicon from a temperature of at least 700° C. to at most 120° C. within a maximum of 2 seconds, and then ground and reacted.

2 Claims, No Drawings

PROCESS FOR THE PREPARATION OF ORGANOCHLOROSILANES

The present invention relates to a process for the preparation of organochlorosilanes by the reaction of rapidly cooled silicon with an alkyl or aryl chloride in the presence of a copper catalyst and promoter substances. The invention in particular relates to a process for the preparation of methylchlorosilanes.

The basic process for the preparation of methylchlorosilanes is the direct reaction of finely ground silicon with methyl chloride in the presence of metallic copper or, more rarely, silver as catalyst. The reaction is known to those skilled in the art as the "Rochow-Synthesis" and is described in U.S. Pat. No. 2,380,995.

This process results mainly in a mixture of the following silanes (Me=CH$_3$): Me$_3$SiCl$_2$, Me$_4$Si, Me$_3$SiCl, MeSiCl$_3$, SiCl$_4$, HSiCl$_3$, MeHSiCl$_2$. Minor quantities of higher boiling compounds such as methylchlorodisilanes, methylchlorotrisilanes, disiloxanes and silomethylenes are formed in addition to the above-mentioned monomeric methylchlorosilanes.

The methylchlorosilanes which are most often used technically are the monomeric compounds and, among these, in particular dimethyldichlorosilane. It is therefore desired to obtain this preferred reaction product as selectively as possible. One measure for this is inter alia the ratio of MeSiCl$_3$/Me$_2$SiCl$_2$ (the so-called Tri-/Di-ratio), whose value should be as small as possible.

Particularly interesting on a large technical scale is the preparation of methylchlorosilanes by the reaction of methyl chloride with silicon in a fluidized bed reactor, in which the methyl chloride used in excess is both a reactant and the fluidizing medium.

Since the basic researches carried out about 40 years ago, there has been a large number of publications describing the processes for carrying out the reaction, for improving the selectivity and for producing suitable catalyst compositions and catalyst/promoter systems. A first comprehensive survey is found, for example, in "Organo-halosilanes: Precursors to Silicones", Voorhoeve, Elsevier Publishing Company Amsterdam, New York, London, 1967.

The most recent works are concentrated mainly on the targeted use of trace elements, so-called promoters, in the catalyst system.

The following are examples: DE-A 3 425 424, EP-A 138 678, EP-A 138 679, DE-A 3 501 085, EP-A 191 502, EP-A 194 214, EP-A 195 728 and EP-A 223 447.

Comparatively few publications deal with silicon and, when they do, they relate mainly to requirements of purity or physical characteristics such as the particle size distribution.

U.S. Pat. No. 3,133,109, for example, mentions that particles sizes of from 20 to 200μ are suitable for optimum operation of a fluidized bed reactor. In U.S. Pat. No. 4,500,724, silicon particles below 700μ are regarded as suitable and it is stated that the average particle size should be from 20 to 300μ, preferably from 100 to 150μ. The above-mentioned limits are regarded as general state of the art values and the man skilled in the art knows well that the optimum in any given case is closely related to the particular reactor system employed.

In U.S. Pat. No. 4,895,969, EP-A 372 918 and EP-A 372 341 it is proposed to use atomized silicon for the synthesis of organochlorosilane. These documents particularly point out the advantageous influence which a rapidly solidified silicon has on the reaction velocity of organochlorosilane synthesis.

In the course of the investigations on which the present invention is based it was found that the thermal tensions produced when silicon is rapidly cooled ("quenched") produce a defect structure which is advantageous for the Rochow synthesis. The more rapid the cooling and the greater the spatial dimensions of the silicon, the greater are the thermal tensions produced. Rapid cooling, however, is inhibited if the spatial dimensions are too great.

The present invention relates to a process for the preparation of organochlorosilanes by the direct reaction of metallic silicon with organyl chlorides, characterized in that metallic silicon is reduced down to particles of at least 5 mm in the smallest dimension and 15 mm in the largest dimension, cooled from a temperature of at least 700° C. to at most 120° C. within a maximum of 2 seconds, subsequently ground and reacted.

Quenching is preferably carried out from a temperature above 900° C.

Quenching may be carried out by immersion of the silicon which is at a high temperature in a liquid which is at a low temperature and is preferably in motion. Liquid nitrogen or water is suitable for this purpose and optionally also other liquids, such as methyl chloride.

Water is preferred since the cost of apparatus is then low and the high specific heat and evaporation enthalpy of water ensure effective cooling.

To prevent the formation of a layer of SiO$_2$ on the silicon and increase the thermal conductivity of water, the water may be specially prepared by the addition of alkaline liquors or additives which have an alkaline or reducing action, e.g. buffer solutions of carbonates, borates, phosphates, organic acids or salts of organic acids, amines, alcohols or hydrazine and its derivatives and/or inorganic, salt-type additives such as chlorides, sulphates, nitrates, etc., or by the addition of surface-active substances such as, for example, fluorine surfactants, alkyl benzene sulphonate or alkyl sulphonate (such as for example Mersolat ® from Bayer AG).

The silicon preferably has a chemical composition (in percent by weight) of from 0.05 to 1% Fe; from 0.01 to 1% Al; from 0.0001 to 1% Ca; from 0 to 8% Cu; from 0 to 1% Zn; from 0 to 1% Sn; from 0 to 0.5% B; from 0 to 0.5% P; from 0 to 0.5% Na; from 0 to 0.5% Li; from 0 to 0.5% K; from 0 to 0.5% Mg; from 0 to 0.5% Sr; from 0 to 0.5% Ba; from 0 to 0.5% Be and the remainder silicon (and possibly small quantities of other impurities).

The silicon more preferably contains from 0.05 to 0.38% Al, from 0.001 to 0.20% Ca and from 0.15 to 0.55% Fe, and most preferably from 0.25 to 0.55% Fe.

After quenching, the silicon is ground in known manner to particle sizes below 1200μ, preferably below 1000μ. After the silicon has been ground it may be converted in known manner into organochlorosilanes by the addition of catalyst and promoter substances if these catalyst and promoter substances are not already present in the silicon of the alloying constituents.

The catalyst used is copper.

Zinc, tin, antimony, arsenic, gallium, indium, phosphorus, lanthanum and/or caesium, and/or compounds thereof are suitable promoter elements. Combinations of two to four promoter substances are preferably used.

On a technical scale, the reaction is preferably carried out in a fluidized bed reactor at temperatures of from 250° to 350° C., preferably from 280° to 330° C. To increase the volume/time yield, the contact between gas and solid may be carried out at an elevated pressure of up to 10 bar.

Methyl chloride is the preferred organyl chloride. If the reaction is to be carried out with other alkyl or aryl chlorides, the deviations well known to the man skilled in the art as regards the optimum reaction temperature and promoter substances should be taken into account.

The invention is described in the examples mentioned below.

Characterizations of the silicon with respect to the Rochow synthesis are carried out in the following experimental arrangement:

The following experiments were all carried out in a stirred bed reactor of glass, internal diameter 30 mm, equipped with a spiral stirrer. The same quantity of silicon having the same particle size distribution of 71 to 160μ was used in each case. Methyl chloride was passed through the catalyst mass from below through a glass flit under a pressure of 2 bar. The quantity of methyl chloride was kept constant and amounted in all cases to about 1.5 l/h at 2 bar. After the reaction mixture had been heated up and the reaction had started, a stationary experimental phase was established at 300° C. and the quantity of crude silane mixture formed per unit time was determined under these specified conditions. The values given are in all cases average values obtained from four individual determinations under constant limiting conditions of 2 bar, 1.5 l/h of methyl chloride and 300° C.

The catalyst mass consisted of 40 g of silicon, 3.2 g of copper catalyst and 0.05 g of ZnO and was homogenized before use. The same catalyst was used in all cases.

EXAMPLE 1

(Comparison)

A silicon containing 0.26% of Fe, 0.18% of Al, 0.039% of Ca and 0.020% of Ti was used.

The silicon was melted under a nitrogen atmosphere and cast to form bars measuring 5 cm×5 cm×20 cm. The silicon was removed from the mold after 18 hours, broken up into pieces and ground. After screening, the silicon was used with a particle size distribution of 71 to 160μ.

The following result was obtained from the Rochow synthesis:

| | |
|---|---|
| Overall production rate | 5.2 g/h |
| $(CH_3)HSiCl_2$ | 2.0% by weight |
| $(CH_3)_3SiCl$ | 2.2% by weight |
| $CH_3SiCl_3$ ("Tri") | 4.9% by weight |
| $(CH_3)_2SiCl_2$ ("Di") | 90.4% by weight |
| % Tri/% Di | 0.054 |
| Polysilanes | 4.4% by weight |

EXAMPLE 2

The silicon which had solidified in bars as in Example 1 was broken down to an average particle size of 8 mm in diameter, heated to 1050° C. under a nitrogen atmosphere, poured from a height of 1 m into ice water which was agitated with a stirrer and then ground. After screening, the silicon was used with a particle size distribution of 71 to 160μ.

The following result was obtained from the Rochow synthesis:

| | |
|---|---|
| Overall production rate | 6.6 g/h |
| $(CH_3)HSiCl_2$ | 1.6% by weight |
| $(CH_3)_3SiCl$ | 2.1% by weight |
| $CH_3SiCl_3$ ("Tri") | 4.1% by weight |
| $(CH_3)_2SiCl_2$ ("Di") | 91.8% by weight |
| % Tri/% Di | 0.045 |
| Polysilanes | 4.0% by weight |

It will be understood that the specification and examples are illustrative but not limitative of the present invention and that other embodiments within the spirit and scope of the invention will suggest themselves to those skilled in the art.

We claim:

1. In the preparation of organochlorosilanes by the direct reaction of metallic silicon with an organyl chloride, the improvement which comprises reducing the metallic silicon particles measuring at least 5 mm in their smallest dimension and 15 mm in their largest dimension, cooling the silicon from temperature of at least about 700° C., to at most 120° C. within a maximum of 2 seconds, then grinding and reacting the silicon.

2. A process according to claim 1, wherein the molten silicon is cooled from temperature above about 900° C.

* * * * *